US008202546B2

(12) United States Patent
Squashic et al.

(10) Patent No.: US 8,202,546 B2
(45) Date of Patent: Jun. 19, 2012

(54) NUTRITIONAL SUPPLEMENT FOR USE UNDER PHYSIOLOGICALLY STRESSFUL CONDITIONS

(75) Inventors: Steven A. Squashic, Scotch Plains, NJ (US); Kevin M. Hudy, Hoboken, NJ (US); David C. Purdy, Freehold, NJ (US)

(73) Assignee: Vertical Pharmaceuticals, Inc., Sayreville, NJ (US)

( * ) Notice: Subject to any disclaimer, the term of this patent is extended or adjusted under 35 U.S.C. 154(b) by 207 days.

(21) Appl. No.: 12/698,174

(22) Filed: Feb. 2, 2010

(65) Prior Publication Data

US 2010/0136104 A1    Jun. 3, 2010

Related U.S. Application Data

(63) Continuation-in-part of application No. 11/197,757, filed on Aug. 4, 2005, now Pat. No. 7,901,710.

(51) Int. Cl.
| A61K 33/26 | (2006.01) |
| A61K 33/34 | (2006.01) |
| A61K 33/32 | (2006.01) |
| A61K 33/06 | (2006.01) |
| A61K 33/04 | (2006.01) |
| A61K 31/28 | (2006.01) |
| A61K 31/04 | (2006.01) |
| A61K 31/295 | (2006.01) |
| A61K 31/30 | (2006.01) |
| A01N 59/16 | (2006.01) |
| A01N 59/20 | (2006.01) |
| A01N 59/06 | (2006.01) |
| A01N 59/02 | (2006.01) |
| A01N 55/02 | (2006.01) |
| A01N 43/08 | (2006.01) |

(52) U.S. Cl. ........ 424/600; 424/630; 424/641; 424/646; 424/682; 424/702; 514/52; 514/167; 514/251; 514/276; 514/458; 514/474; 514/492; 514/500; 514/502; 514/725; 514/904

(58) Field of Classification Search .................. None
See application file for complete search history.

(56) References Cited

U.S. PATENT DOCUMENTS

| 3,258,846 A | 7/1966 | Powell, Jr. |
| 4,582,709 A | 4/1986 | Peters et al. |
| 4,629,625 A | 12/1986 | Gaull |
| 4,752,479 A | 6/1988 | Briggs et al. |
| 4,786,510 A | 11/1988 | Nakel et al. |
| 4,786,518 A | 11/1988 | Nakel et al. |
| 4,812,303 A | 3/1989 | Iorio |
| 4,867,989 A | 9/1989 | Silva et al. |
| 4,973,467 A | 11/1990 | Sahley |
| 4,980,168 A | 12/1990 | Sahley |
| 4,992,282 A | 2/1991 | Mehansho et al. |
| 4,994,283 A | 2/1991 | Mehansho et al. |
| 5,021,424 A | 6/1991 | Lawton-Wall |
| 5,051,258 A | 9/1991 | Sahley |
| 5,061,723 A | 10/1991 | Barua et al. |
| 5,151,274 A | 9/1992 | Saltman et al. |
| 5,223,285 A | 6/1993 | DeMichele et al. |
| 5,308,627 A | 5/1994 | Umbdenstock, Jr. |
| 5,312,626 A | 5/1994 | Gergely et al. |
| 5,332,579 A | 7/1994 | Umbdenstock |
| 5,445,837 A | 8/1995 | Burkes et al. |
| 5,447,732 A | 9/1995 | Tanimoto et al. |
| 5,468,506 A | 11/1995 | Andon |
| 5,494,678 A | 2/1996 | Paradissis et al. |
| 5,496,567 A | 3/1996 | McLean |
| 5,501,857 A | 3/1996 | Zimmer |
| 5,514,382 A | 5/1996 | Sultenfuss |
| 5,562,869 A | 10/1996 | Drahos et al. |
| 5,569,458 A | 10/1996 | Greenberg |
| 5,569,459 A | 10/1996 | Shlyankevich |
| 5,569,477 A | 10/1996 | Nesbitt |
| 5,571,441 A | 11/1996 | Andon et al. |
| 5,597,585 A | 1/1997 | Williams et al. |
| 5,612,061 A | 3/1997 | Rabkin |
| 5,614,553 A | 3/1997 | Ashmead et al. |
| 5,626,883 A | 5/1997 | Paul |
| 5,646,116 A | 7/1997 | Burk |
| 5,654,011 A | 8/1997 | Jackson et al. |
| 5,675,789 A | 10/1997 | Ishii et al. |
| 5,686,107 A | 11/1997 | Ratnaraj et al. |

(Continued)

OTHER PUBLICATIONS

Ansel (Pharmaceutical Dosage Forms and Drug Delivery Systems 1999, 7th Ed. Lippincott Williams & Wilkins; pp: 90-91, 179 and 346-348).*

Pressman (The Complete Idiot's Guide to Vitamins and Minerals 1997, NY, pp. 5, 7, 8, 20, 25, 46-50, 289 and 293).*

Magnesium Factsheet, [online] Office of Dietary Supplements, National Institute of Health, Jan. 2005, Retrieved from the internet Jul. 7, 2009,http://web.archive.org/web/20050212015808/http://ods.od.nih.gov/factsheets/magnesium.asp, 13 pages.

*Primary Examiner* — Ernst Arnold

(74) *Attorney, Agent, or Firm* — Maldjian Law Group LLC; John P. Maldjian, Esq.; Christopher Wen, Esq.

(57) ABSTRACT

In one embodiment of the present invention, a pharmaceutically-acceptable single-dosage formulation consists essentially of about 300 mg of vitamin C; about 1200 IUs of vitamin D3; about 125 IUs of vitamin E; about 25 mg of vitamin B1; about 3.4 mg of vitamin B2; about 35 mg of niacin; about 35 mg of vitamin B6; about 1.25 mg of folate; about 70 mcg of vitamin B12; about 5 mg of pantothenic acid; about 300 mcg of biotin; about 50 mg of calcium; about 35 mg of magnesium; about 35 mg of zinc; about 1 mg of copper; about 125 mcg of selenium; about 150 mcg of chromium; about 25 mg of alpha lipoic acid; about 35 mg of co-enzyme Q-10; about 2 mg of lutein; about 500 mcg of lycopene; about 5 mg of pepper extract; and at least one or more excipients.

20 Claims, No Drawings

U.S. PATENT DOCUMENTS

| | | |
|---|---|---|
| D393,203 S | 4/1998 | Saltzman et al. |
| 5,770,215 A | 6/1998 | Moshyedi |
| 5,775,652 A | 7/1998 | Crawshaw et al. |
| 5,807,586 A | 9/1998 | Jackson et al. |
| 5,869,084 A | 2/1999 | Paradissis et al. |
| 5,879,698 A | 3/1999 | Ellenbogen et al. |
| 5,922,361 A | 7/1999 | Bieser et al. |
| 5,922,704 A | 7/1999 | Bland |
| 5,935,610 A | 8/1999 | McLean |
| 5,948,443 A | 9/1999 | Riley et al. |
| 5,952,317 A | 9/1999 | Deluca et al. |
| 5,962,030 A | 10/1999 | Fine |
| 5,965,162 A | 10/1999 | Fuisz et al. |
| 5,971,334 A | 10/1999 | Crawshaw et al. |
| 5,976,568 A | 11/1999 | Riley |
| 5,976,784 A | 11/1999 | DeLuca et al. |
| 5,977,073 A | 11/1999 | Khaled |
| 6,040,333 A | 3/2000 | Jackson |
| 6,051,236 A | 4/2000 | Portman |
| 6,060,093 A | 5/2000 | Davis et al. |
| 6,080,431 A | 6/2000 | Andon et al. |
| 6,080,788 A | 6/2000 | Sole et al. |
| 6,086,915 A | 7/2000 | Zeligs et al. |
| 6,106,874 A | 8/2000 | Liebrecht et al. |
| 6,112,240 A | 8/2000 | Pogue et al. |
| 6,124,268 A | 9/2000 | Ghosal |
| 6,143,300 A | 11/2000 | Stevenot |
| 6,150,399 A | 11/2000 | Patel et al. |
| 6,150,411 A | 11/2000 | Stordy |
| 6,174,857 B1 | 1/2001 | Burk |
| 6,174,890 B1 | 1/2001 | Riga et al. |
| 6,187,318 B1 | 2/2001 | Mitchell et al. |
| 6,190,693 B1 | 2/2001 | Kafrissen et al. |
| 6,197,329 B1 | 3/2001 | Hermelin et al. |
| 6,203,819 B1 | 3/2001 | Fine |
| 6,210,686 B1 | 4/2001 | Bell et al. |
| 6,228,388 B1 | 5/2001 | Paradissis et al. |
| 6,235,322 B1 | 5/2001 | Lederman |
| 6,238,672 B1 | 5/2001 | Chen |
| 6,241,997 B1 | 6/2001 | Kershman et al. |
| 6,245,378 B1 | 6/2001 | Cavazza |
| 6,248,909 B1 | 6/2001 | Akimoto et al. |
| 6,255,341 B1 | 7/2001 | DeMichele et al. |
| 6,258,846 B1 | 7/2001 | Hermelin et al. |
| 6,261,600 B1 | 7/2001 | Kirschner et al. |
| 6,265,438 B1 | 7/2001 | Steward |
| 6,277,396 B1 | 8/2001 | Dente |
| 6,290,974 B1 | 9/2001 | Swaisgood et al. |
| 6,291,517 B1 | 9/2001 | Bagchi et al. |
| 6,291,533 B1 | 9/2001 | Fleischner |
| 6,299,886 B1 | 10/2001 | Piper |
| 6,299,896 B1 | 10/2001 | Cooper et al. |
| 6,300,309 B1 | 10/2001 | Guler et al. |
| 6,346,284 B1 | 2/2002 | Briend et al. |
| 6,352,713 B1 | 3/2002 | Kirschner et al. |
| 6,358,544 B1 | 3/2002 | Henry, Jr. et al. |
| 6,358,925 B1 | 3/2002 | Guler et al. |
| 6,361,800 B1 | 3/2002 | Cooper et al. |
| 6,362,221 B1 | 3/2002 | Clark et al. |
| 6,365,176 B1 | 4/2002 | Bell et al. |
| 6,368,640 B1 | 4/2002 | Wuh et al. |
| 6,369,042 B1 | 4/2002 | Oberthur et al. |
| 6,372,782 B1 | 4/2002 | Patel et al. |
| 6,410,058 B2 | 6/2002 | Gohlke et al. |
| 6,416,737 B1 | 7/2002 | Manolagas et al. |
| 6,420,350 B1 | 7/2002 | Fleischner |
| 6,426,097 B2 | 7/2002 | Grose |
| 6,432,442 B1 | 8/2002 | Buehler et al. |
| 6,436,406 B1 | 8/2002 | Yegorova |
| 6,436,453 B1 | 8/2002 | van Lengerich et al. |
| 6,436,910 B1 | 8/2002 | Yerxa et al. |
| 6,440,450 B1 | 8/2002 | Han et al. |
| 6,444,218 B2 | 9/2002 | Han et al. |
| 6,447,809 B1 | 9/2002 | Krumhar et al. |
| 6,451,341 B1 | 9/2002 | Slaga et al. |
| 6,455,068 B1 | 9/2002 | Licari |
| 6,455,714 B1 | 9/2002 | Holick et al. |
| 6,461,652 B1 | 10/2002 | Henry et al. |
| 6,465,013 B1 | 10/2002 | DeBernardi |
| 6,468,568 B1 | 10/2002 | Leusner et al. |
| 6,475,511 B2 | 11/2002 | Gohlke et al. |
| 6,475,539 B1 | 11/2002 | DeWille et al. |
| 6,479,545 B1 | 11/2002 | Levinson et al. |
| 6,485,738 B1 | 11/2002 | Huang et al. |
| 6,488,956 B1 | 12/2002 | Paradissis et al. |
| 6,495,173 B1 | 12/2002 | Yegorova |
| 6,495,177 B1 | 12/2002 | deVries et al. |
| 6,495,736 B1 | 12/2002 | Brunkow et al. |
| 6,497,885 B2 | 12/2002 | Trant |
| 6,497,906 B1 | 12/2002 | Kelly |
| 6,503,529 B1 | 1/2003 | Fleischner |
| 6,509,045 B2 | 1/2003 | Henry et al. |
| 6,509,326 B1 | 1/2003 | Andon et al. |
| 6,517,861 B2 | 2/2003 | Singh et al. |
| 6,521,247 B1 | 2/2003 | deVries |
| 6,541,005 B1 | 4/2003 | Yegorova |
| 6,541,006 B1 | 4/2003 | Yegorova |
| 6,544,525 B1 | 4/2003 | Yegorova |
| 6,544,563 B2 | 4/2003 | Wuh et al. |
| 6,562,378 B1 | 5/2003 | Chandra |
| 6,565,891 B1 | 5/2003 | Chandra |
| 6,569,445 B2 | 5/2003 | Manning et al. |
| 6,569,477 B2 | 5/2003 | Lederman |
| 6,569,857 B1 | 5/2003 | Hermelin et al. |
| 6,569,869 B2 | 5/2003 | Assmann et al. |
| 6,576,242 B1 | 6/2003 | Yegorova |
| 6,576,253 B2 | 6/2003 | Manning et al. |
| 6,576,666 B2 | 6/2003 | Hermelin et al. |
| 6,579,544 B1 | 6/2003 | Rosenberg et al. |
| 6,579,899 B1 | 6/2003 | Wurtman et al. |
| 6,585,998 B2 | 7/2003 | Cartwright et al. |
| 6,592,863 B2 | 7/2003 | Fuchs et al. |
| 6,592,909 B2 | 7/2003 | Belcheff |
| 6,593,310 B1 | 7/2003 | Cullis-Hill |
| 6,596,313 B2 | 7/2003 | Rosenbloom |
| 6,596,762 B2 | 7/2003 | Sokol |
| 6,605,646 B2 | 8/2003 | Herbert |
| 6,630,158 B2 | 10/2003 | Popp et al. |
| 6,642,212 B1 | 11/2003 | Kelly |
| 6,646,013 B1 | 11/2003 | Barker et al. |
| 6,649,195 B1 | 11/2003 | Gorsek |
| 6,653,332 B2 | 11/2003 | Jaen et al. |
| 6,660,293 B2 | 12/2003 | Giordano et al. |
| 6,667,063 B2 | 12/2003 | Crum |
| 6,706,478 B2 | 3/2004 | Duff et al. |
| 6,720,013 B2 | 4/2004 | Johnson et al. |
| 6,743,770 B2 | 6/2004 | Bell et al. |
| 6,752,986 B2 | 6/2004 | Bauer et al. |
| 6,756,401 B2 | 6/2004 | Day et al. |
| 6,780,438 B2 | 8/2004 | Gohlke et al. |
| 6,790,462 B2 | 9/2004 | Hendricks |
| 6,793,935 B2 | 9/2004 | Hermelin et al. |
| 6,797,077 B2 | 9/2004 | Pearl |
| 6,814,983 B2 | 11/2004 | Giordano et al. |
| 6,818,228 B1 | 11/2004 | Walsdorf et al. |
| 6,818,234 B1 | 11/2004 | Nair et al. |
| 6,827,945 B2 | 12/2004 | Rosenbloom |
| 6,830,761 B1 | 12/2004 | Zlotkin |
| 6,835,402 B1 | 12/2004 | Clark et al. |
| 6,837,682 B2 | 1/2005 | Evenson et al. |
| 6,843,372 B2 | 1/2005 | Weinstein |
| 6,844,012 B1 | 1/2005 | Forceville et al. |
| 6,849,274 B1 | 2/2005 | Whittle |
| 6,849,613 B2 | 2/2005 | Prasad et al. |
| 6,852,335 B2 | 2/2005 | DeBernardi et al. |
| 6,863,904 B2 | 3/2005 | Giordano et al. |
| 6,881,419 B2 | 4/2005 | Lovett |
| 6,881,425 B2 | 4/2005 | Pushpangadan et al. |
| 6,887,850 B2 | 5/2005 | Fuchs et al. |
| 6,914,073 B2 | 7/2005 | Boulos et al. |
| 6,929,807 B1 | 8/2005 | McAnalley et al. |
| 6,953,588 B2 | 10/2005 | Cooper et al. |
| 6,955,873 B1 | 10/2005 | Blum |
| 6,960,581 B2 | 11/2005 | Betageri et al. |
| 6,995,166 B1 | 2/2006 | Giordano et al. |
| 2001/0022980 A1 | 9/2001 | Bell et al. |
| 2001/0031283 A1 | 10/2001 | Belcheff |

| | | |
|---|---|---|
| 2001/0031744 A1 | 10/2001 | Kosbab |
| 2001/0036468 A1 | 11/2001 | Han et al. |
| 2001/0036936 A1 | 11/2001 | Day et al. |
| 2001/0041741 A1 | 11/2001 | Sole et al. |
| 2001/0055623 A1 | 12/2001 | Jackson |
| 2002/0015762 A1 | 2/2002 | Quinlan |
| 2002/0032234 A1 | 3/2002 | Hermelin et al. |
| 2002/0034543 A1 | 3/2002 | Kirschner et al. |
| 2002/0037928 A1 | 3/2002 | Jaen et al. |
| 2002/0044957 A1 | 4/2002 | Fuchs et al. |
| 2002/0044961 A1 | 4/2002 | Kirschner et al. |
| 2002/0044988 A1 | 4/2002 | Fuchs et al. |
| 2002/0045184 A1 | 4/2002 | Chen |
| 2002/0058088 A1 | 5/2002 | Henry et al. |
| 2002/0064578 A1 | 5/2002 | Henry et al. |
| 2002/0066691 A1 | 6/2002 | Varon |
| 2002/0069197 A1 | 6/2002 | Katayama et al. |
| 2002/0099032 A1 | 7/2002 | Higashi et al. |
| 2002/0102330 A1 | 8/2002 | Schramm et al. |
| 2002/0110604 A1 | 8/2002 | Babish et al. |
| 2002/0116249 A1 | 8/2002 | Ellinger et al. |
| 2002/0119183 A1 | 8/2002 | Hermelin et al. |
| 2002/0119928 A1 | 8/2002 | McAnalley |
| 2002/0119933 A1 | 8/2002 | Butler et al. |
| 2002/0132800 A1 | 9/2002 | Popp et al. |
| 2002/0136711 A1 | 9/2002 | Cochran |
| 2002/0136782 A1 | 9/2002 | Fleischner |
| 2002/0137749 A1 | 9/2002 | Levinson et al. |
| 2002/0146471 A1 | 10/2002 | Wuh et al. |
| 2002/0147152 A1 | 10/2002 | Bell et al. |
| 2002/0147153 A1 | 10/2002 | Bell et al. |
| 2002/0150607 A1 | 10/2002 | Schramm et al. |
| 2002/0150649 A1 | 10/2002 | Bell |
| 2002/0155163 A1 | 10/2002 | Benjamin et al. |
| 2002/0155181 A1 | 10/2002 | Wuh et al. |
| 2002/0168429 A1 | 11/2002 | Mann |
| 2002/0172721 A1 | 11/2002 | Boulos et al. |
| 2002/0173510 A1 | 11/2002 | Levinson et al. |
| 2002/0187205 A1 | 12/2002 | Paradissis et al. |
| 2002/0193379 A1 | 12/2002 | Copp et al. |
| 2002/0197330 A1 | 12/2002 | Jackson et al. |
| 2003/0012824 A1 | 1/2003 | Ott et al. |
| 2003/0012826 A1 | 1/2003 | Giordano et al. |
| 2003/0013639 A1 | 1/2003 | Yurchak et al. |
| 2003/0017205 A1 | 1/2003 | DeBernardi |
| 2003/0031726 A1 | 2/2003 | Hendricks |
| 2003/0044473 A1 | 3/2003 | Fleischner |
| 2003/0059481 A1 | 3/2003 | Krumhar et al. |
| 2003/0068372 A1 | 4/2003 | Kirschner et al. |
| 2003/0091552 A1 | 5/2003 | Cartwright et al. |
| 2003/0091613 A1 | 5/2003 | DeWille et al. |
| 2003/0096018 A1 | 5/2003 | Schloss et al. |
| 2003/0099730 A1 | 5/2003 | Rosenbloom |
| 2003/0104050 A1* | 6/2003 | Matharu et al. ............... 424/465 |
| 2003/0104078 A1 | 6/2003 | Barrett-Reis et al. |
| 2003/0108594 A1 | 6/2003 | Manning et al. |
| 2003/0108605 A1 | 6/2003 | Hermelin et al. |
| 2003/0108624 A1 | 6/2003 | Kosbab |
| 2003/0138484 A1 | 7/2003 | Gianesello et al. |
| 2003/0143287 A1 | 7/2003 | Bell |
| 2003/0147996 A1 | 8/2003 | Prasad et al. |
| 2003/0148946 A1 | 8/2003 | Levy et al. |
| 2003/0149765 A1 | 8/2003 | Hubbard et al. |
| 2003/0162807 A1 | 8/2003 | Day et al. |
| 2003/0166247 A1 | 9/2003 | Brunkow et al. |
| 2003/0170327 A1 | 9/2003 | Dahl |
| 2003/0185918 A1 | 10/2003 | Rosenbloom |
| 2003/0190355 A1 | 10/2003 | Hermelin et al. |
| 2003/0190369 A1 | 10/2003 | Lovett |
| 2003/0198661 A1 | 10/2003 | Harper et al. |
| 2003/0198730 A1 | 10/2003 | Stewart |
| 2003/0202992 A1 | 10/2003 | Fuchs et al. |
| 2003/0203053 A1 | 10/2003 | Wuh et al. |
| 2003/0206969 A1 | 11/2003 | Nidamarty et al. |
| 2003/0216351 A1 | 11/2003 | Hermelin et al. |
| 2003/0229014 A1 | 12/2003 | Schneider et al. |
| 2004/0009535 A1 | 1/2004 | Brunkow et al. |
| 2004/0013743 A1 | 1/2004 | Jackson |
| 2004/0039504 A1 | 2/2004 | Coffee et al. |
| 2004/0047898 A1 | 3/2004 | Harper et al. |
| 2004/0048812 A1 | 3/2004 | Kelly |
| 2004/0048870 A1 | 3/2004 | Amir et al. |
| 2004/0052918 A1 | 3/2004 | Briend et al. |
| 2004/0058321 A1 | 3/2004 | Brunkow et al. |
| 2004/0076664 A1 | 4/2004 | Bonura |
| 2004/0082536 A1 | 4/2004 | Cooper et al. |
| 2004/0086574 A1 | 5/2004 | Giordano et al. |
| 2004/0087515 A1 | 5/2004 | Butler et al. |
| 2004/0101554 A1 | 5/2004 | Kirschner et al. |
| 2004/0106561 A1 | 6/2004 | Kelly |
| 2004/0109901 A1 | 6/2004 | Giordano et al. |
| 2004/0140241 A1 | 7/2004 | Weinstein |
| 2004/0162292 A1 | 8/2004 | Evenstad et al. |
| 2004/0166175 A1 | 8/2004 | Giordano et al. |
| 2004/0170702 A1 | 9/2004 | VanStockum |
| 2004/0175415 A1 | 9/2004 | Chan et al. |
| 2004/0185119 A1 | 9/2004 | Theuer |
| 2004/0191296 A1 | 9/2004 | Sternberg |
| 2004/0197430 A1 | 10/2004 | Meyrowitz |
| 2004/0198674 A1 | 10/2004 | Levy et al. |
| 2004/0209848 A1 | 10/2004 | Maruyama et al. |
| 2004/0213857 A1 | 10/2004 | Soldati et al. |
| 2004/0213873 A1 | 10/2004 | Parvez |
| 2004/0219235 A1 | 11/2004 | Pushpangadan et al. |
| 2004/0220118 A1 | 11/2004 | Bland et al. |
| 2004/0224032 A1 | 11/2004 | Zlotkin |
| 2004/0228931 A1 | 11/2004 | Chokshi et al. |
| 2004/0234544 A1 | 11/2004 | Jager et al. |
| 2004/0234579 A1 | 11/2004 | Finke |
| 2004/0235728 A1 | 11/2004 | Stoch et al. |
| 2004/0254095 A1 | 12/2004 | Martin et al. |
| 2004/0259886 A1 | 12/2004 | Day et al. |
| 2005/0009835 A1 | 1/2005 | Thomas |
| 2005/0016893 A1 | 1/2005 | Nakagawa et al. |
| 2005/0026223 A1 | 2/2005 | Manolagas et al. |
| 2005/0032741 A1 | 2/2005 | Venkataraman |
| 2005/0037065 A1 | 2/2005 | Kirschner et al. |
| 2005/0058671 A1 | 3/2005 | Bedding et al. |
| 2005/0059641 A1 | 3/2005 | Ray et al. |
| 2005/0069608 A1 | 3/2005 | Hendricks |
| 2005/0095262 A1 | 5/2005 | Camponovo et al. |
| 2005/0100613 A1 | 5/2005 | Giordano et al. |
| 2005/0101670 A1 | 5/2005 | Hermelin et al. |
| 2005/0106266 A1 | 5/2005 | Levinson et al. |
| 2005/0112176 A1 | 5/2005 | Dopson et al. |
| 2005/0112177 A1 | 5/2005 | Dopson et al. |
| 2005/0112211 A1 | 5/2005 | Gervais et al. |
| 2005/0119218 A1 | 6/2005 | Prasad et al. |
| 2005/0123628 A1 | 6/2005 | Zabrecky |
| 2005/0130933 A1 | 6/2005 | Jacobs et al. |
| 2005/0142124 A1 | 6/2005 | Kaiser |
| 2005/0143357 A1 | 6/2005 | Pousette et al. |
| 2005/0153019 A1 | 7/2005 | Fuchs et al. |
| 2005/0171034 A1 | 8/2005 | Halevie-Goldman |
| 2005/0186252 A1 | 8/2005 | Ahlgren et al. |
| 2005/0187144 A1 | 8/2005 | Fine et al. |
| 2005/0196343 A1 | 9/2005 | Reddy et al. |
| 2005/0196434 A1 | 9/2005 | Brierre |
| 2005/0196469 A1 | 9/2005 | Thys-Jacobs |
| 2005/0198239 A1 | 9/2005 | Hughes |
| 2005/0214383 A1 | 9/2005 | Bubnis et al. |
| 2005/0214388 A1 | 9/2005 | Gorham et al. |
| 2005/0226942 A1 | 10/2005 | Myhill et al. |
| 2005/0233946 A1 | 10/2005 | Fine et al. |
| 2005/0233947 A1 | 10/2005 | Fine et al. |
| 2005/0249787 A1 | 11/2005 | Reynolds et al. |
| 2005/0249788 A1 | 11/2005 | Reynolds et al. |
| 2005/0256178 A1 | 11/2005 | Eggersdorfer et al. |
| 2005/0260284 A1 | 11/2005 | DiMateeo-Leggio |
| 2005/0261172 A1 | 11/2005 | Schneider et al. |
| 2005/0261257 A1 | 11/2005 | Vermeer |
| 2005/0281888 A1 | 12/2005 | Chandra |
| 2005/0281889 A1 | 12/2005 | Chandra |
| 2005/0282794 A1 | 12/2005 | Fine et al. |
| 2005/0286646 A1 | 12/2005 | Fails et al. |
| 2005/0287228 A1 | 12/2005 | Trant |
| 2005/0289279 A1 | 12/2005 | Fails et al. |
| 2005/0289379 A1 | 12/2005 | Teutsch et al. |

| | | |
|---|---|---|
| 2006/0003981 A1 | 1/2006 | Fine et al. |
| 2006/0008543 A1 | 1/2006 | Myhill et al. |
| 2006/0008544 A1 | 1/2006 | Myhill et al. |
| 2006/0018975 A1 | 1/2006 | Talbott |
| 2006/0024384 A1 | 2/2006 | Giordano |
| 2006/0024409 A1 | 2/2006 | Giordano |
| 2006/0034912 A1 | 2/2006 | Giordano et al. |
| 2006/0034916 A1 | 2/2006 | Giordano et al. |
| 2006/0160753 A1 | 7/2006 | Cassidy et al. |

* cited by examiner

NUTRITIONAL SUPPLEMENT FOR USE UNDER PHYSIOLOGICALLY STRESSFUL CONDITIONS

CROSS-REFERENCE TO RELATED APPLICATIONS

The present application is a continuation-in-part of U.S. patent application Ser. No. 11/197,757, filed Aug. 4, 2005, entitled "Nutritional Supplement for Use under Physiologically Stressful Conditions," the disclosure of which is incorporated herein by reference in its entirety.

BACKGROUND OF THE INVENTION

1. Field of the Invention

Embodiments of the present invention generally relate to nutritional supplements and in particular to nutritional supplements for use under physiologically stressful conditions.

2. Description of the Related Art

Physiological responses to stressful conditions are generally the same; only the intensity of the response and whether or not any given response will be evoked are individual in nature. Acute stressful situations, such as resulting from a trauma, produce a physiological response, after which the body returns to its normal, un-stressful state. When the body enters a stressful situation, the sympathetic nervous system invokes a fight or flight response. Once the stressful stimuli have been removed, the parasympathetic nervous system returns the body to a normal state.

Chronic stressful conditions, caused by for example a divorce, an unpleasant boss, lack of money, or building a new home, are more insidious. The physiological response endures and the body fails to return to the baseline state. Being in a continuous state of stress, an individual will feel unwell, partly because the mechanisms that ordinarily help overcome stress have become exhausted. That is, the parasympathetic nervous system is unable to return the body to a "normal" state.

Symptoms classically seen in a stressful situation include an increase in heart rate, blood pressure, sweating, metabolic rate and peristaltic activity. These symptoms can be alleviated by inducing the body to return to its normal resting state.

Thus, there is a need for a nutritional supplement to alleviate or at least reduce the stress and symptoms associated therewith.

SUMMARY OF THE INVENTION

Embodiments of the present invention generally relate to nutritional supplements and in particular to nutritional supplements for use under physiologically stressful conditions.

In one embodiment, a pharmaceutically-acceptable single-dosage formulation consists essentially of between about 150 mg to about 450 mg of vitamin C; between about 600 IUs to about 1800 IUs of vitamin D3; between about 75 IUs to about 150 IUs of vitamin E; between about 15 mg to about 35 mg of vitamin B1; between about 1.7 mg to about 5.1 mg of vitamin B2; between about 20 mg to about 50 mg of niacin; between about 20 mg to about 50 mg of vitamin B6; between about 0.5 mg to about 2.5 mg of folate; between about 35 mcg to about 105 mcg of vitamin B12; between about 2.5 mg to about 7.5 mg of pantothenic acid; between about 150 mcg to about 450 mcg of biotin; between about 50 mg to about 100 mg of calcium; between about 15 mg to about 55 mg of magnesium; between about 15 mg to about 55 mg of zinc; between about 0.5 to about 1.5 mg of copper; between about 75 mcg to about 175 mcg of selenium; between about 75 mcg to about 225 mcg of chromium; between about 10 mg to about 40 mg of alpha lipoic acid; between about 20 mg to about 50 mg of co-enzyme Q-10; between about 1 mg to about 3 mg of lutein; between about 250 mcg to about 750 mcg of lycopene; between about 2.5 mg to about 7.5 mg of pepper extract; and at least one or more excipients.

In another embodiment of the present invention, a pharmaceutically-acceptable single-dosage formulation consists of between about 150 mg to about 450 mg of ascorbic acid; between about 600 IUs to about 1800 IUs of cholecalciferol; between about 75 IUs to about 150 IUs of d-alpha tocopherol succinate; between about 15 mg to about 35 mg of thiamine mononitrate; between about 1.7 mg to about 5.1 mg of riboflavin; between about 20 mg to about 50 mg of niacinamide; between about 20 mg to about 50 mg of pyridoxine hcl; between about 0.5 mg to about 2.5 mg of folic acid; between about 35 mcg to about 105 mcg of cyanocobalamin; between about 2.5 mg to about 7.5 mg of d-calcium pantothenate; between about 150 mcg to about 450 mcg of d-biotin; between about 50 mg to about 100 mg of dicalcium malate; between about 15 mg to about 55 mg of dimagnesium malate; between about 15 mg to about 55 mg of zinc bisglycinate chelate; between about 0.5 to about 1.5 mg of copper amino acid chelate; between about 75 mcg to about 175 mcg of selenium amino acid chelate; between about 75 mcg to about 225 mcg of chromium amino acid chelate; between about 10 mg to about 40 mg of alpha lipoic acid; between about 20 mg to about 50 mg of co-enzyme Q-10; between about 1 mg to about 3 mg of lutein; between about 250 mcg to about 750 mcg of lycopene; between about 2.5 mg to about 7.5 mg of pepper extract; and at least one or more excipients.

In yet another embodiment of the present invention, a pharmaceutically-acceptable single-dosage formulation consists of between about 150 mg to about 450 mg of ascorbic acid; between about 600 IUs to about 1800 IUs of cholecalciferol; between about 75 IUs to about 150 IUs of d-alpha tocopherol succinate; between about 15 mg to about 35 mg of thiamine mononitrate; between about 1.7 mg to about 5.1 mg of riboflavin; between about 20 mg to about 50 mg of niacinamide; between about 20 mg to about 50 mg of pyridoxine hcl; between about 0.5 mg to about 2.5 mg of folic acid; between about 35 mcg to about 105 mcg of cyanocobalamin; between about 2.5 mg to about 7.5 mg of d-calcium pantothenate; between about 150 mcg to about 450 mcg of d-biotin; between about 50 mg to about 100 mg of dicalcium malate; between about 15 mg to about 55 mg of dimagnesium malate; between about 15 mg to about 55 mg of zinc bisglycinate chelate; between about 0.5 to about 1.5 mg of copper amino acid chelate; between about 75 mcg to about 175 mcg of selenium amino acid chelate; between about 75 mcg to about 225 mcg of chromium amino acid chelate; between about 10 mg to about 40 mg of alpha lipoic acid; between about 20 mg to about 50 mg of co-enzyme Q-10; between about 1 mg to about 3 mg of lutein; between about 250 mcg to about 750 mcg of lycopene; between about 2.5 mg to about 7.5 mg of pepper extract; between about 100 mg to about 300 mg of dicalcium phosphate; between about 25 mg to about 75 mg of microcrystalline cellulose; between about 10 mg to about 30 mg of stearic acid; between about 10 mg to about 30 mg of croscarmellose sodium; between about 5 mg to about 15 mg of magnesium trisillicate; between about 5 mg to about 15 mg of magnesium stearate; and between about 5 mg to about 15 mg of hydroxypropyl methylcellulose; wherein the single-dosage formulation comprises at one of a pill, a tablet, a caplet, a capsule, a chewable tablet, a quick dissolve tablet, an effervescent tablet, a hard gelatin capsule, a soft gelatin capsule, a liquid suspension or a food product.

DETAILED DESCRIPTION

It is understood that the embodiments of the present invention are not limited to the particular methodologies, protocols, solvents and reagents, and the like, described herein as they may vary. It is also to be understood the terminology used herein is used for the purpose of describing particular embodiments only and not intended to limit the scope of the present invention. It must also be noted that as used herein and in the appended claims, the singular form "a," "an" and "the" include the plural reference unless the context clearly dictates otherwise. Thus, for example, a reference to "a vitamin" is a reference to one or more vitamins and includes equivalents thereof know to those skilled in the art and so forth.

Unless defined otherwise, all technical and scientific terms used herein have the same meaning as commonly understood by one of ordinary skilled in the art to which this invention belongs. Preferred methods, devices and materials are described, although any methods and materials similar or equivalent to those described herein could be used in the practice or testing of the present invention. All references cited herein are incorporated by reference herein in there entirety.

The term "disease state" as used herein, may comprise any state in which one or more organs or components of an organism malfunction. The term includes "disease state" may refer to any deterioration of any component of a body. The term "disease state" may refer to any deficiency of any compound necessary for the maintenance or function of any component of any organism. The term "disease state" may refer to any condition in which a body contains toxins, produced by microorganisms that infect the body or by body cells through faulty metabolism or absorbed from an external source.

The term "disease states" may be adverse states caused by any diet, any virus, or any bacteria. "Disease states" may comprise disorders associated with pregnant females such as for example, osteomalacia and preeclampsia and disorders associated with a fetus such as, for example, neurotube defects and various fetal abnormalities. "Disease states" may comprise any pulmonary disorder such as, for example, bronchitis, bronchiectasis, atelectasis, pneumonia, diseases caused by inorganic dust, diseases caused by organic dust, any pulmonary fibrosis, and pleurisy. "Disease states" may comprise any hematological/oncological disorders such as, for example, anemia, hemophilia, leukemia, lymphoma.

A "disease state" may comprise any cancer such as, for example, breast cancer, lung cancer, prostate cancer, pancreatic cancer, liver cancer, stomach cancer, testicular cancer, ovarian cancer, skin cancer, cancer of the brain, cancer of the mouth, cancer of the throat, and cancer of the neck. "Disease states" may comprise any disorder of the immune system such as, for example, Acquired Immune Deficiency Syndrome (AIDS), AIDS-related complex, infection by any strain of any Human Immunodeficiency Virus (HIV), and other viruses and pathogens such as bacteria.

A "disease state" may comprise any cardiovascular disorders such as, for example, arterial hypertension, orthostatic hypotension, arteriolosclerosis, coronary artery disease, cardiomyopathy, any arrhythmia, any valvular heart disease, endocarditis, pericardial disease, any cardiac tumor, any aneurism, and any peripheral vascular disorder. "Disease states" may comprise any hepatic/biliary disorders such as, for example, jaundice, hepatic steatosis, fibrosis, cirrhosis, hepatitis, any hepatic granuloma, any liver tumor, cholelithiasis, cholecystitis, and choledocholithiasis.

The term "physiologically stressful state," as used herein, comprises any state of an organism in which the organism faces one or more physiological challenges. A "physiologically stressful state" may comprise pre-pregnancy, pregnancy, lactation, or conditions in which an organism faces physiological challenges related to for example, elevated metabolic demand, increased plasma volume, or decreased concentrations of nutrient-binding proteins. A "physiologically stressful state" may result from one or more disease states.

The term "subject" as used herein comprises any and all organisms and includes the term "patient." "Subject" may refer to a human or any other animal. "Subject" may also refer to a fetus.

Embodiments of the present invention relate to a nutritional supplement, which contains active ingredients to relieve an individual in a physiological stressful condition. One embodiment of the present invention assembles clinically proven food-grade nutrients in efficacious doses shown to relieve the symptoms of physiological stressful conditions. Specifically, the nutritional supplement comprises fat-soluble and water-soluble vitamins as well as essential minerals, in certain amounts, to reduce physiological stressful conditions associated with the individual as discussed below.

Physiological responses to physiological stressful conditions are the same regardless of the causation. Under stressful situations, the body releases neurotransmitters (e.g., epinephrine, norepinephrine and serotonin) and cortisol to bring the body back to a non-stressed state. In a chronically stressed situation, the neurotransmitters can become depleted and as a result, the lack of serotonin is directly related to poor mood and depression. Cortisol, however, does not get depleted and its continued presence in the body depresses mood. Long-term exposure to cortisol leads to impaired memory, depressed immune function, chronic obesity and development of chronic disease.

The nutritional supplement can be made in a variety of forms such as a pharmaceutical composition (e.g., table, powder, suspension, liquid, capsule, and gel), nutritional beverages, puddings, confections (i.e., candy), ice cream, frozen confections and novelties, or non-baked extruded food such as bars to assist patients with stressful conditions and the management thereof. The nutritional supplement can be formulated into a snack to be taken as part of a diet or it can be formulated as a meal replacement. For a snack and meal replacement, nutritional supplements should provide from about 50 to about 400 kcal per serving.

For purposes of the present invention, an embodiment of the nutritional supplement comprises the components described about as a single serving (serving unit), whereby one or a plurality (in one embodiment: two) of these supplements is (are) consumed daily. The proportions of these N ingredients are based on about 60 to about 75-gram serving. The preferred form of administration is in tablet form but the supplement could be consumed as a nutritional bar or as a liquid.

In an embodiment, each serving contains 220 kcal and is comprised of macro nutrient percentages in concert with the dietary recommendation of the American Diabetic Association and American Dietary Association. Other serving sizes are contemplated by the present invention. The total amount of each ingredient should be appropriately adjusted.

The ingredients that make up the nutritional supplement are described in detail below with regard to their relative role each contributes to the therapeutic advantages of the present invention.

Vitamin E, a fat-soluble vitamin, is an antioxidant vitamin involved in the metabolism of all cells. It protects vitamin A and essential fatty acids from oxidation in the body cells and prevents breakdown of body tissues. Embodiments of the present invention may comprise between about 75 IUs to about 150 IUs of vitamin E, and in one embodiment, about 125 IUs of vitamin E are provided. In one exemplary embodiment, vitamin E is provided in the form of d-alpha tocopherol succinate.

Vitamin D3 is a naturally occurring bodily substance that many believe exert a protective effect in multiple sclerosis—both in the development of the disease and in limiting its progression. It is naturally produced in the skin in response to sunlight but is also present in certain foodstuffs (particularly oily fish). Vitamin D3 is a type of steroid hormone and among other things, a powerful mediator of immune function.

Vitamin D3 is best known for its effect on calcium metabolism. Proper levels are necessary to maintain bone mineral density and serum (blood) calcium levels. This is especially true among the very young where it is used to treat rickets and in combination with vitamin A for the treatment of osteoporosis in the elderly, particularly post menopausal women who are often subject to fractures due to loss of bone density.

In studies, vitamin D3 has been found helpful against autoimmunity for the down-regulation of Th1 and up-regulation of Th2 cells. It has also been shown to regulate the neurotrophins NGF (Nerve Growth Factor), NT-3 (NeuroTrophin 3) and NT-4. In addition, vitamin D3 has also been found to promote differentiation and cell death in neuroblastoma (brain tumor) cell lines as well as cancers in general.

Embodiments of the present invention may comprise between about 600 IUs to about 1800 IUs of vitamin D3, and in one embodiment, about 1200 IUs of vitamin D3 are provided. In one exemplary embodiment, vitamin D3 is provided in the form of cholecalciferol.

Vitamin C is a water-soluble, antioxidant vitamin. It is important in forming collagen, a protein that gives structure to bones, cartilage, muscle, and blood vessels. Vitamin C also aids in the absorption of iron, and helps maintain capillaries, bones, and teeth. As a water-soluble antioxidant, vitamin C is in a unique position to "scavenge" aqueous peroxyl radicals before these destructive substances have a chance to damage lipids. It works along with vitamin E, a fat-soluble antioxidant, and the enzyme glutathione peroxidase to stop free radical chain reactions.

Vitamin C can enhance the body's resistance to an assortment of diseases, including infectious disorders and many types of cancer. It strengthens and protects the immune system by stimulating the activity of antibodies and immune system cells such as phagocytes and neutrophils. Vitamin C contributes to a variety of other biochemical functions. These include the biosynthesis of the amino acid carnitine and the catecholamines that regulate the nervous system. It also helps the body to absorb iron and to break down histamine. Although vitamin C is found in every cell, it is especially useful in key parts of the body. These include the blood, the skin, the nervous system, the teeth and bones and glands such as the thymus, adrenals and thyroid.

Embodiments of the present invention may comprise between about 150 mg to about 450 mg of vitamin C, and in one embodiment, about 300 mg of vitamin C are provided. In one exemplary embodiment, vitamin C is provided in the form of ascorbic acid.

Vitamin B1, also known as thiamin, helps fuel your body by converting blood sugar into energy. It keeps the mucous membranes healthy and is essential for nervous system, cardiovascular and muscular function. Vitamin B1 (thiamin) is essential for the metabolism of carbohydrates to produce energy and for normal nerve and heart function. Embodiments of the present invention may comprise between about 15 mg to about 35 mg of vitamin B1, and in one embodiment, about 25 mg of vitamin B1 are provided. In one exemplary embodiment, vitamin B1 is provided in the form of thiamine mononitrate.

Vitamin B2 is a water-soluble vitamin in the B-complex group. Generally, riboflavin, a form of vitamin B2, works with the other B vitamins. It is important for body growth and red blood cell production and helps in releasing energy from carbohydrates. Riboflavin, as flavin mononucleotide or flavin adenine dinucleotide, acts as an essential coenzyme in many oxidation-reduction reactions involved with carbohydrate metabolism. Deficiency results in oral, ocular, cutaneous, and genital lesions. Embodiments of the present invention may comprise between about 1.7 mg to about 5.1 mg of vitamin B2, and in one embodiment, about 3.4 mg of vitamin B2 are provided.

Niacin, or vitamin B3, is required for cell respiration, helps in the release of energy and metabolism of carbohydrates, fats, and proteins, proper circulation and healthy skin, functioning of the nervous system, and normal secretion of bile and stomach fluids. It is used in the synthesis of sex hormones, treating schizophrenia and other mental illnesses, and a memory-enhancer. Niacin given in pharmaceutical dosage improves the blood cholesterol profile, and has been used to clear the body of organic poisons, such as certain insecticides. Embodiments of the present invention may comprise between about 20 mg to about 50 mg of niacin, and in one embodiment, about 35 mg of niacin are provided. In one exemplary embodiment, niacin is provided in the form of niacinamide.

Folate is a water-soluble vitamin in the B-complex group. Generally, folic acid, a form of folate, works along with vitamin B12 and vitamin C to help the body digest and utilize proteins and to synthesize new proteins when they are needed. It is necessary for the production of red blood cells and for the synthesis of DNA. Folic acid also helps with tissue growth and cell function. In addition, it helps to increase appetite when needed and stimulates the formation of digestive acids.

Folic acid supplements may be used in the treatment of disorders associated with folic acid deficiency and may also be part of the recommended treatment for certain menstrual problems and leg ulcers. Embodiments of the present invention may comprise between about 0.5 mg to about 2.5 mg of folate, and in one embodiment, about 1.25 mg of folate are provided.

Vitamin B6 is a water-soluble vitamin that exists in three major chemical forms: pyridoxine, pyridoxal, and pyridoxamine. It performs a wide variety of functions in the body and is essential for good health. For example, vitamin B6 is needed for more than 100 enzymes involved in protein metabolism. It is also essential for red blood cell metabolism. The nervous and immune systems need vitamin B6 to function efficiently, and it is also needed for the conversion of tryptophan to niacin.

The body needs vitamin B6 to make hemoglobin. Hemoglobin within red blood cells carries oxygen to tissues. Vitamin B6 also helps increase the amount of oxygen carried by hemoglobin. A vitamin B6 deficiency can result in a form of anemia that is similar to iron deficiency anemia. Vitamin B6 also helps maintain blood glucose (sugar) within a normal range. When caloric intake is low, the body needs vitamin B6 to help convert stored carbohydrate or other nutrients to glucose to maintain normal blood sugar levels.

Embodiments of the present invention may comprise between about 20 mg to about 50 mg of vitamin B6, and in one embodiment, about 35 mg of vitamin B6 are provided. In one exemplary embodiment, vitamin B6 is provided in the form of pyridoxine.

Biotin, a water-soluble member of the B-vitamin family, is an essential nutrient in human nutrition. It is involved in the biosynthesis of fatty acids, gluconeogenesis, energy production, the metabolism of the branched-chain amino acids (L-leucine, L-isoleucine, L-valine) and the de novo synthesis of purine nucleotides. Research indicates that biotin plays a role in gene expression, both at the transcriptional and translational levels, and that it may also play a role in DNA replication. Biotin is necessary for both metabolism and growth in humans, particularly with reference to production of fatty acids, antibodies, digestive enzymes, and niacin (vitamin B3) metabolism.

Embodiments of the present invention may comprise between about 150 mcg to about 450 mcg of vitamin B1, and in one embodiment, about 300 mcg of biotin are provided. In one exemplary embodiment, biotin is provided in the form of d-biotin.

Pantothenic acid, also known as vitamin B5, is essential for a number of basic bodily functions, from growth to reproduction. It participates in the continual breakdown of carbohydrates, fats, and proteins from food, converting them into compounds the body can use. This vitamin also produces numerous enzymes and helps maintain precise communication between the central nervous system and the brain. Pantothenic acid comes in two forms: calcium pantothenate and pantethine. Calcium pantothenate is widely used for treating ailments from stress to heartburn, while pantethine is mainly recommended for lowering blood cholesterol levels in those who don't respond to other natural treatments.

Embodiments of the present invention may comprise between about 2.5 mg to about 7.5 mg of pantothenic acid, and in one embodiment, about 5 mg of pantothenic acid are provided. In one exemplary embodiment, pantothenic acid is provided in the form of d-calcium pantothenate.

Vitamin B12, a water-soluble vitamin, is also called cobalamin because it contains the metal cobalt. This vitamin helps maintain healthy nerve cells and red blood cells. It is also needed to help make DNA, the genetic material in all cells. Embodiments of the present invention may comprise between about 35 mcg to about 105 mcg of vitamin B12, and in one embodiment, about 70 mcg of vitamin B12 are provided. In one exemplary embodiment, vitamin B12 is provided in the form of cyanocobalamin.

Calcium is an important component of a healthy diet and a mineral necessary for life. Approximately ninety-nine percent of the body's calcium is stored in the bones and teeth. The rest of the calcium in the body has other important uses, such as some exocytosis, especially neurotransmitter release, and muscle contraction. In the electrical conduction system of the heart, calcium replaces sodium as the mineral that depolarizes the cell, proliferating the action potential.

Long-term calcium deficiency can lead to rickets and poor blood clotting and in case of a menopausal woman, it can lead to osteoporosis, in which the bone deteriorates and there is an increased risk of fractures. While a lifelong deficit can affect bone and tooth formation, over-retention can cause hypercalcemia (elevated levels of calcium in the blood), and decreased absorption of other minerals. However, a high calcium intake has been associated with a lower risk for kidney stones. Thus, a proper balance of calcium absorption in the body is requisite for good health.

Embodiments of the present invention may comprise between about 50 mg to about 100 mg of calcium, and in one embodiment, about 75 mg of calcium are provided. In one exemplary embodiment, vitamin B12 is provided in the form of dicalcium malate. In another embodiment, dicalcium malate may be obtained in the form of a supplement, from Albion International, Inc. of Clearfield, Utah, sold under the commercial brand DimaCal®.

Magnesium is the fourth most abundant mineral in the body and is essential to good health. Approximately 50% of total body of magnesium is found in the bone. The other half is found predominantly inside cells of body tissues and organs. Only 1% of magnesium is found in blood, but the body works very hard to keep blood levels of magnesium constant. Magnesium is needed for more than 300 biochemical reactions in the body. It helps maintain normal muscle and nerve function, keeps heart rhythm steady, supports a healthy immune system, and keeps bones strong. Magnesium also helps regulate blood sugar levels, promotes normal blood pressure, and is known to be involved in energy metabolism and protein synthesis. Magnesium may play a role in preventing and managing disorders such as hypertension, cardiovascular disease, and diabetes.

Embodiments of the present invention may comprise between about 15 mg to about 55 mg of magnesium, and in one embodiment, about 35 mg of magnesium are provided. In one exemplary embodiment, magnesium is provided in the form of dimagnesium malate.

Zinc is vital for the healthy working of many of the body's systems. Zinc plays a crucial role in growth and cell division where it is required for protein and DNA synthesis, in insulin activity, in the metabolism of the ovaries and testes, and in liver function. As a component of many enzymes, zinc is involved in the metabolism of proteins, carbohydrates, lipids and energy. Zinc helps with the healing of wounds and is a vital component of many enzyme reactions. It is also important for healthy skin and is essential for a healthy immune system and resistance to infection.

Embodiments of the present invention may comprise between about 15 mg to about 55 mg of zinc, and in one embodiment, about 35 mg of zinc are provided. In one exemplary embodiment, zinc is provided in the form of zinc bisglycinate chelate.

Selenium is a trace mineral essential to good health. Selenium is incorporated into proteins to make selenoproteins, which are important antioxidant enzymes. The antioxidant properties of selenoproteins help prevent cellular damage from free radicals that may contribute to the development of chronic diseases such as cancer and heart disease. Other selenoproteins help regulate thyroid function and play a role in the immune system.

Embodiments of the present invention may comprise between about 75 mcg to about 175 mcg of selenium, and in one embodiment, about 125 mcg of selenium are provided. In one exemplary embodiment, selenium is provided in the form of selenium amino acid chelate.

Chromium is a mineral required in small quantities by the body. It enables insulin to function normally and helps the body metabolize carbohydrates and fats. Picolinate, a by-product of the amino acid tryptophan, is paired with chromium in supplements because it helps the body absorb chromium more efficiently. Embodiments of the present invention may comprise between about 75 mcg to about 225 mcg of chromium, and in one embodiment, about 150 mcg of chromium are provided. In one exemplary embodiment, chromium is provided in the form of chromium amino acid chelate.

Copper is needed for normal growth and health. Copper is also needed to help the body use iron. It is also important for nerve function, bone growth, and to help the body use sugar. Embodiments of the present invention may comprise between about 0.5 mg to about 1.5 mg of copper, and in one embodiment, about 1 mg of copper is provided. In one exemplary embodiment, copper is provided in the form of copper amino acid chelate.

Alpha-lipoic acid, also known as thioctic acid, is a disulfide compound that is a cofactor in vital energy-producing reactions in the body. It is also a potent biological antioxidant in both the fatty and watery regions of cells. Alpha-lipoic acid also plays an important role in the synergism of antioxidants, recycling and extending the metabolic lifespan of vitamin C, glutathione, coenzyme Q10, and vitamin E. Embodiments of the present invention may comprise between about 10 mg to about 40 mg of alpha-lipoic acid, and in one embodiment, about 25 mg of alpha-lipoic acid are provided.

Co-enzyme Q10 is often utilized as a dietary supplement because of its ability to transfer electrons and therefore act as an antioxidant. Supplementation of Co-enzyme Q10 is a treatment for some of the very rare and serious mitochondrial disorders and other metabolic disorders. Coenzyme Q10 is also beneficial in treatment of patients with congestive heart failure, and as a relief from symptoms associated with migraine headaches, cancer treatments (e.g., chemotherapy, radiation, etc.), cardiac arrest, and blood pressure, among others. Embodiments of the present invention may comprise between about 20 mg to about 50 mg of co-enzyme Q10, and in one embodiment, about 35 mg of co-enzyme Q10 are provided.

Lutein is a member of the carotenoid family, a family best known for betacarotene. Lutein is a natural fat-soluble yellowish pigment found in the macula of the human retina, as well as the human crystalline lens. It is thought to play a role in protection against age-related macular degeneration (ARMD) and age-related cataract formation. Lutein may also be protective against some forms of cancer. Embodiments of the present invention may comprise between about 1 mg to about 3 mg of lutein, and in one embodiment, about 2 mg of lutein are provided.

Lycopene is a member of the carotenoid family of chemical substances. Lycopene is a natural fat-soluble pigment and antioxidant that may be beneficial in treating certain disorders, such as prostate cancer and other cancers, coronary heart disease, exercise-induced asthma, macular degeneration, sunburn, atherosclerosis, high cholesterol, and high blood pressure associated with pregnancy. Embodiments of the present invention may comprise between about 250 mcg to about 750 mcg of lycopene, and in one embodiment, about 500 mcg of lycopene are provided.

Natural pepper extract may provide enhanced absorption of nutrients by the digestive system. In many embodiments, a natural pepper extract may comprise an extract from the fruits of *piper nigrum* L (i.e., household black pepper) or *piper longum* L (i.e., long pepper). In one exemplary embodiment, the pepper extract comprises an extract manufactured by Sabinsa Corporation, commercially known as Peperine or Bioperine, covered by U.S. Pat. Nos. 5,536,506, 5,544,161, 5,972,382 and 6,054,585, the disclosures of which are incorporated by reference in their entireties. Embodiments of the present invention may comprise between about 2.5 mg to about 7.5 mg of pepper extract, and in one embodiment, about 5 mg of pepper extract are provided.

While the above elements comprise the essential vitamins, minerals and nutrients of embodiments of the present invention, the nutritional supplement can also contain other ingredients, provided such ingredients to not materially or substantially alter the embodiments of the present invention.

In many embodiments of the present invention, the nutritional supplement further comprises at least one or more excipients, or other inactive ingredients, to be used as carriers for the active ingredients of the formulation. In one embodiment, the nutritional supplement may further comprise at least one or more of dicalcium phosphate, microcrystalline cellulose, stearic acid, croscarmellose sodium, magnesium trisillicate, magnesium stearate, hydroxypropyl methylcellulose, or the like.

In certain embodiments, the excipients may be provided to the formulation in amounts of between about 100 mg to about 300 mg of dicalcium phosphate, between about 25 mg to about 75 mg of microcrystalline cellulose, between about 10 mg to about 30 mg of stearic acid, between about 10 mg to about 30 mg of croscarmellose sodium, between about 5 mg to about 15 mg of magnesium trisillicate, between about 5 mg to about 15 mg of magnesium stearate, and between about 5 mg to about 15 mg of hydroxypropyl methylcellulose. In one specific embodiment, the excipients are provided to the formulation in the amounts of about 200 mg of dicalcium phosphate, about 50 mg of microcrystalline cellulose, about 20 mg of stearic acid, about 20 mg of croscarmellose sodium, about 10 mg of magnesium trisillicate, about 10 mg of magnesium stearate and about 10 mg of hydroxypropyl methylcellulose.

In addition to excipients or carriers, other inactive ingredients may also be provided in reasonable amounts, such as flavoring agents, coloring agents, or the like. The amount of the other inactive ingredients per unit serving are a matter of design and will depend upon the total number of unit servings of the nutritional supplement daily administered to the patient. The total amount of other ingredients will also depend, in part, upon the condition of the patient. Preferably the amount of other ingredients will be a fraction or multiplier of the recommended daily allowance (RDA) or RDI (reference daily intake) amounts. For example, nutritional supplements can comprise 50 percent RDI of vitamins and minerals per unit dosage and the patient will consume two units per day.

Flavors, coloring agents, spices, nuts and the like can be incorporated into the product. Flavorings can be in the form of flavored extracts, volatile oils, chocolate flavorings (e.g., non-caffeinated cocoa or chocolate or chocolate substitute such as carob), peanut butter flavoring, cookie crumbs, crisp rice, vanilla or any commercially available flavoring. Flavoring can be protected with mixed tocopherols.

Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract or volatile oils, such as balm oil, bay oil or bergamots oil, cedar-wood oil, cherry oil, walnut oil, cinnamon oil, clove oil, or peppermint oil; peanut butter, chocolate flavoring, vanilla cookie crumb, butterscotch or toffee.

In an embodiment, nutritional supplement contains berry or other fruit flavors. The food compositions may further be coated, for example with a yoghurt coating, if it is produced as a bar.

Emulsifiers may be added for stability of the final product. Examples of suitable emulsifiers include, but are not limited to, lecithin (e.g., from egg or soy), and/or mono-n dye-glycerides. Other emulsifiers are readily apparent to the skilled artesian and selection of suitable emulsifiers will depend, in part, on the formulation and final nutritional supplement.

Preservatives may also be added to the nutritional supplement to extend product shelf life. Preferably, preservatives such as potassium sorbate, sodium sorbate, potassium benzonate, sodium benzonate or calcium disodium EDTA are used.

The nutritional supplements of embodiments of the present invention may be formulated using any pharmaceutically acceptable forms of the vitamins, minerals and other nutrients discussed above, including their salts. They may be formulated into capsules, tablets, powders, suspensions, jells or liquids optionally comprising at physiologically acceptable carrier such as but not limited to water, milk, juice, sodas, starch, vegetable oils, salt solutions, hydroxymethyl cellulose, carbohydrates.

In an embodiment, bio-nutritional supplements may be formulated as a tablet. The nutritional supplements of this invention may be formulated with other foods or liquids to provide pre-measured supplemental foods, such as a single serving bar or beverage, for example. To manufacture such a beverage, the ingredients are dried and made readily soluble in water and other consumable liquids as described above.

Several of the complex actions initiated by a stressful condition are dependent on a constant supply of certain nutrients. Lack of these nutrients often causes poor adaptation to the stressful condition and a failure to return to homeostasis. The most comprehensive work on this subject is the report from the Committee on Military Nutrition Research of the Institute of Medicine in response to the Armed Forces request for a list of nutrients that will enhance performance during stressful conditions. (Marriott B M (ed.), Food Components to Enhance Performance, Washington, D.C.: National Academy Press (1994): Committee on Military Nutrition and Research, Conclusions and Recommendations, in: Marriott B N. Food Components to Enhance Performance, Washington, D.C.: National Academy Press, 47-61, 1994)).

The active ingredients of a nutritional supplement of the present invention, as discussed in detail above, work to relieve stressful conditions and alter the mood.

Long-term administration of the nutritional supplements of the present invention may aid in the reduction of health risks associated with chronic stress, such as diminished mental and physical performance, dampened immune function, depression, hyper lididemia, cardiovascular disease, hypertension, obesity and diabetes. Regulation of serotonin and cortisol levels using the nutritional supplement in the present invention may be instrumental in reducing some of the side effects of stress.

The composition and dietary nutritional supplements of the present invention are, in one embodiment, orally administered daily. Based on the serving size of about 60 grams to about 75 grams per serving, the recommended dosage is twice daily. For example, the supplement is in the form of a tablet and the patient would consume one in the morning and one mid to late afternoon, to modulate stress and mood, which can be impaired by foods consumed at lunch. The recommended daily amounts of each ingredient, as described above, serve as a guideline for formulating the dietary supplements of this present invention. The actual amounts of each ingredient per unit dosage will depend on the number of units daily administered to the individual in need thereof. This is a matter of product design and is well within the skill of the dietary supplement formulator.

The ingredients can be administered in a single formulation or they can be separately administered. For example, it may be desirable to administer bitter tasting ingredients in the form that masks their tastes (e.g., capsule or pill form) rather than incorporating them into the nutritional composition itself (e.g., powder or bar). Thus, an embodiment of the present invention also provides a pharmaceutical pack or one or more containers filled with one or more of the ingredients of the nutritional compositions of the invention (e.g., nutritional supplement in the form of a powder and tablets).

While the invention has been particularly shown and described with reference to embodiments thereof, it will be understood by those skilled in the art that various changes in form and details may be made therein without departing from the scope of the present invention encompassed by the appended claims.

What is claimed is:

1. A pharmaceutically-acceptable single-dosage formulation, consisting essentially of:
   between about 150 mg to about 450 mg of vitamin C;
   between about 600 IUs to about 1800 IUs of vitamin D3;
   between about 75 IUs to about 150 IUs of vitamin E;
   between about 15 mg to about 35 mg of vitamin B1;
   between about 1.7 mg to about 5.1 mg of vitamin B2;
   between about 20 mg to about 50 mg of niacin;
   between about 20 mg to about 50 mg of vitamin B6;
   between about 0.5 mg to about 2.5 mg of folate;
   between about 35 mcg to about 105 mcg of vitamin B12;
   between about 2.5 mg to about 7.5 mg of pantothenic acid;
   between about 150 mcg to about 450 mcg of biotin;
   between about 50 mg to about 100 mg of calcium;
   between about 15 mg to about 55 mg of magnesium;
   between about 15 mg to about 55 mg of zinc;
   between about 0.5 to about 1.5 mg of copper;
   between about 75 mcg to about 175 mcg of selenium;
   between about 75 mcg to about 225 mcg of chromium;
   between about 10 mg to about 40 mg of alpha lipoic acid;
   between about 20 mg to about 50 mg of co-enzyme Q-10;
   between about 1 mg to about 3 mg of lutein;
   between about 250 mcg to about 750 mcg of lycopene;
   between about 2.5 mg to about 7.5 mg of pepper extract; and
   at least one or more excipients.

2. The pharmaceutically-acceptable single-dosage formulation of claim 1, wherein the formulation consists essentially of:
   about 300 mg of vitamin C;
   about 1200 IUs of vitamin D3;
   about 125 IUs of vitamin E;
   about 25 mg of vitamin B1;
   about 3.4 mg of vitamin B2;
   about 35 mg of niacin;
   about 35 mg of vitamin B6;
   about 1.25 mg of folate;
   about 70 mcg of vitamin B12;
   about 5 mg of pantothenic acid;
   about 300 mcg of biotin;
   about 75 mg of calcium;
   about 35 mg of magnesium;
   about 35 mg of zinc;
   about 1 mg of copper;
   about 125 mcg of selenium;
   about 150 mcg of chromium;
   about 25 mg of alpha lipoic acid;
   about 35 mg of co-enzyme Q-10;
   about 2 mg of lutein;
   about 500 mcg of lycopene;
   about 5 mg of pepper extract; and
   at least one or more excipients.

3. The formulation of claim 1, wherein the single-dosage formulation is administered in a form selected from the group consisting of a pill, a tablet, a caplet, a capsule, a chewable tablet, a quick dissolve tablet, an effervescent tablet, a hard gelatin capsule, and a soft gelatin capsule.

4. The formulation of claim 3, wherein the single-dosage formulation is administered in a form with an enteric coating.

5. The formulation of claim 1, wherein the single-dosage formulation is administered in the form of a liquid suspension.

6. The formulation of claim 1, wherein the single-dosage formulation is administered in the form of a food product.

7. The formulation of claim 1, wherein the excipients consist essentially of at least one of dicalcium phosphate, microcrystalline cellulose, stearic acid, croscarmellose sodium, magnesium trisillicate, magnesium stearate or hydroxypropyl methylcellulose.

8. The formulation of claim 1, wherein the at least one or more excipients consist of:
between about 100 mg to about 300 mg of dicalcium phosphate;
between about 25 mg to about 75 mg of microcrystalline cellulose;
between about 10 mg to about 30 mg of stearic acid;
between about 10 mg to about 30 mg of croscarmellose sodium;
between about 5 mg to about 15 mg of magnesium trisillicate;
between about 5 mg to about 15 mg of magnesium stearate; and
between about 5 mg to about 15 mg of hydroxypropyl methylcellulose.

9. The formulation of claim 8, wherein the at least one or more excipients consist of:
about 200 mg of dicalcium phosphate;
about 50 mg of microcrystalline cellulose;
about 20 mg of stearic acid;
about 20 mg of croscarmellose sodium;
about 10 mg of magnesium trisillicate;
about 10 mg of magnesium stearate; and
about 10 mg of hydroxypropyl methylcellulose.

10. A pharmaceutically-acceptable single-dosage formulation, consisting of:
between about 150 mg to about 450 mg of ascorbic acid;
between about 600 IUs to about 1800 IUs of cholecalciferol;
between about 75 IUs to about 150 IUs of d-alpha tocopherol succinate;
between about 15 mg to about 35 mg of thiamine mononitrate;
between about 1.7 mg to about 5.1 mg of riboflavin;
between about 20 mg to about 50 mg of niacinamide;
between about 20 mg to about 50 mg of pyridoxine hcl;
between about 0.5 mg to about 2.5 mg of folic acid;
between about 35 mcg to about 105 mcg of cyanocobalamin;
between about 2.5 mg to about 7.5 mg of d-calcium pantothenate;
between about 150 mcg to about 450 mcg of d-biotin;
between about 50 mg to about 100 mg of dicalcium malate;
between about 15 mg to about 55 mg of dimagnesium malate;
between about 15 mg to about 55 mg of zinc bisglycinate chelate;
between about 0.5 to about 1.5 mg of copper amino acid chelate;
between about 75 mcg to about 175 mcg of selenium amino acid chelate;
between about 75 mcg to about 225 mcg of chromium amino acid chelate;
between about 10 mg to about 40 mg of alpha lipoic acid;
between about 20 mg to about 50 mg of co-enzyme Q-10;
between about 1 mg to about 3 mg of lutein;
between about 250 mcg to about 750 mcg of lycopene;
between about 2.5 mg to about 7.5 mg of pepper extract; and
at least one or more excipients.

11. The pharmaceutically-acceptable single-dosage formulation of claim 10, wherein the formulation consists of:
about 300 mg of ascorbic acid
about 1200 IUs of cholecalciferol;
about 125 IUs of d-alpha tocopherol succinate;
about 35 mg of thiamine mononitrate;
about 5.1 mg of riboflavin;
about 50 mg of niacinamide;
about 50 mg of pyridoxine hcl;
about 2.5 mg of folic acid;
about 105 mcg of cyanocobalamin;
about 7.5 mg of d-calcium pantothenate;
about 450 mcg of d-biotin;
about 75 mg of dicalcium malate;
about 55 mg of dimagnesium malate;
about 55 mg of zinc bisglycinate chelate;
about 1.5 mg of copper amino acid chelate;
about 175 mcg of selenium amino acid chelate;
about 225 mcg of chromium amino acid chelate;
about 40 mg of alpha lipoic acid;
about 50 mg of co-enzyme Q-10;
about 3 mg of lutein;
about 750 mcg of lycopene;
about 7.5 mg of pepper extract; and
at least one or more excipients.

12. The formulation of claim 10, wherein the single-dosage formulation is administered in a form selected from the group consisting of a pill, a tablet, a caplet, a capsule, a chewable tablet, a quick dissolve tablet, an effervescent tablet, a hard gelatin capsule, and a soft gelatin capsule.

13. The formulation of claim 12, wherein the single-dosage formulation is administered in a form with an enteric coating.

14. The formulation of claim 10, wherein the single-dosage formulation is administered in the form of a liquid suspension.

15. The formulation of claim 10, wherein the single-dosage formulation is administered in the form of a food product.

16. The formulation of claim 10, wherein the excipients consist of at least one of dicalcium phosphate, microcrystalline cellulose, stearic acid, croscarmellose sodium, magnesium trisillicate, magnesium stearate or hydroxypropyl methylcellulose.

17. The formulation of claim 10, wherein the at least one or more excipients consist of:
between about 100 mg to about 300 mg of dicalcium phosphate;
between about 25 mg to about 75 mg of microcrystalline cellulose;
between about 10 mg to about 30 mg of stearic acid;
between about 10 mg to about 30 mg of croscarmellose sodium;
between about 5 mg to about 15 mg of magnesium trisillicate;
between about 5 mg to about 15 mg of magnesium stearate; and between about 5 mg to about 15 mg of hydroxypropyl methylcellulose.

18. The formulation of claim 17, wherein the at least one or more excipients consist of:
- about 200 mg of dicalcium phosphate;
- about 50 mg of microcrystalline cellulose;
- about 20 mg of stearic acid;
- about 20 mg of croscarmellose sodium;
- about 10 mg of magnesium trisillicate;
- about 10 mg of magnesium stearate; and
- about 10 mg of hydroxypropyl methylcellulose.

19. A pharmaceutically-acceptable single-dosage formulation, consisting of:
- between about 150 mg to about 450 mg of ascorbic acid;
- between about 600 IUs to about 1800 IUs of cholecalciferol;
- between about 75 IUs to about 150 IUs of d-alpha tocopherol succinate;
- between about 15 mg to about 35 mg of thiamine mononitrate;
- between about 1.7 mg to about 5.1 mg of riboflavin;
- between about 20 mg to about 50 mg of niacinamide;
- between about 20 mg to about 50 mg of pyridoxine hcl;
- between about 0.5 mg to about 2.5 mg of folic acid;
- between about 35 mcg to about 105 mcg of cyanocobalamin;
- between about 2.5 mg to about 7.5 mg of d-calcium pantothenate;
- between about 150 mcg to about 450 mcg of d-biotin;
- between about 50 mg to about 100 mg of dicalcium malate;
- between about 15 mg to about 55 mg of dimagnesium malate;
- between about 15 mg to about 55 mg of zinc bisglycinate chelate;
- between about 0.5 to about 1.5 mg of copper amino acid chelate;
- between about 75 mcg to about 175 mcg of selenium amino acid chelate;
- between about 75 mcg to about 225 mcg of chromium amino acid chelate;
- between about 10 mg to about 40 mg of alpha lipoic acid;
- between about 20 mg to about 50 mg of co-enzyme Q-10;
- between about 1 mg to about 3 mg of lutein;
- between about 250 mcg to about 750 mcg of lycopene;
- between about 2.5 mg to about 7.5 mg of pepper extract;
- between about 100 mg to about 300 mg of dicalcium phosphate;
- between about 25 mg to about 75 mg of microcrystalline cellulose;
- between about 10 mg to about 30 mg of stearic acid;
- between about 10 mg to about 30 mg of croscarmellose sodium;
- between about 5 mg to about 15 mg of magnesium trisillicate;
- between about 5 mg to about 15 mg of magnesium stearate; and
- between about 5 mg to about 15 mg of hydroxypropyl methylcellulose;

wherein the single-dosage formulation is administered in a form selected from a group consisting of a pill, a tablet, a caplet, a capsule, a chewable tablet, a quick dissolve tablet, an effervescent tablet, a hard gelatin capsule, a soft gelatin capsule, a liquid suspension or a food product.

20. The pharmaceutically-acceptable single-dosage formulation of claim 19, wherein the formulation consists of:
- about 300 mg of ascorbic acid
- about 1200 IUs of cholecalciferol;
- about 125 IUs of d-alpha tocopherol succinate;
- about 35 mg of thiamine mononitrate;
- about 5.1 mg of riboflavin;
- about 50 mg of niacinamide;
- about 50 mg of pyridoxine hcl;
- about 2.5 mg of folic acid;
- about 105 mcg of cyanocobalamin;
- about 7.5 mg of d-calcium pantothenate;
- about 450 mcg of d-biotin;
- about 75 mg of dicalcium malate;
- about 55 mg of dimagnesium malate;
- about 55 mg of zinc bisglycinate chelate;
- about 1.5 mg of copper amino acid chelate;
- about 175 mcg of selenium amino acid chelate;
- about 225 mcg of chromium amino acid chelate;
- about 40 mg of alpha lipoic acid;
- about 50 mg of co-enzyme Q-10;
- about 3 mg of lutein;
- about 750 mcg of lycopene;
- about 7.5 mg of pepper extract;
- about 200 mg of dicalcium phosphate;
- about 50 mg of microcrystalline cellulose;
- about 20 mg of stearic acid;
- about 20 mg of croscarmellose sodium;
- about 10 mg of magnesium trisillicate;
- about 10 mg of magnesium stearate; and
- about 10 mg of hydroxypropyl methylcellulose.

* * * * *